US012391797B2

(12) United States Patent
Hiraga et al.

(10) Patent No.: US 12,391,797 B2
(45) Date of Patent: Aug. 19, 2025

(54) FLUOROPOLYETHER GROUP CONTAINING COMPOUND AND METHOD FOR PRODUCING THE SAME

(71) Applicant: DAIKIN INDUSTRIES, LTD., Osaka (JP)

(72) Inventors: Kentarou Hiraga, Osaka (JP); Akinari Sugiyama, Osaka (JP); Fumihiko Yamaguchi, Osaka (JP); Takashi Nomura, Osaka (JP); Shouta Shibutani, Osaka (JP); Shingo Okuno, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 719 days.

(21) Appl. No.: 17/692,474

(22) Filed: Mar. 11, 2022

(65) Prior Publication Data

US 2022/0235177 A1 Jul. 28, 2022

Related U.S. Application Data

(63) Continuation of application No. PCT/JP2020/032914, filed on Aug. 31, 2020.

(30) Foreign Application Priority Data

Sep. 13, 2019 (JP) ................................ 2019-167534
Jan. 22, 2020 (JP) ................................ 2020-008580

(51) Int. Cl.
*C08G 65/02* (2006.01)
*C08G 65/00* (2006.01)
*C08G 65/18* (2006.01)
*C08G 65/26* (2006.01)
*C07C 69/34* (2006.01)

(52) U.S. Cl.
CPC .......... *C08G 65/007* (2013.01); *C08G 65/18* (2013.01); *C08G 65/26* (2013.01); *C07C 69/34* (2013.01); *C08G 65/02* (2013.01)

(58) Field of Classification Search
CPC ......... C08G 65/26; C08G 65/02; C08G 65/18
See application file for complete search history.

(56) References Cited

U.S. PATENT DOCUMENTS

| | | | | | |
|---|---|---|---|---|---|
| 3,250,808 A | * | 5/1966 | Milian, Jr. | ............... | C10M 3/00 564/201 |
| 4,131,740 A | * | 12/1978 | England | ................. | C07C 59/60 562/583 |
| 4,138,426 A | * | 2/1979 | England | ................. | C07C 59/60 558/449 |
| 4,247,713 A | * | 1/1981 | England | ............. | C08G 65/2639 560/192 |
| 4,334,082 A | * | 6/1982 | Resnick | ................ | C07C 255/00 558/449 |
| 4,357,282 A | * | 11/1982 | Anderson | ............... | C07C 51/58 560/174 |
| 4,390,720 A | * | 6/1983 | Resnick | ................ | C07C 69/708 560/183 |
| 4,845,268 A | * | 7/1989 | Ohsaka | ................ | C08G 65/223 562/587 |
| 4,904,417 A | * | 2/1990 | Ohsaka | ............. | C08G 65/3236 562/583 |
| 4,973,742 A | * | 11/1990 | Ohsaka | ................ | C08G 65/223 560/179 |
| 5,506,309 A | * | 4/1996 | Bierschenk | ........ | C08G 65/3236 528/417 |
| 5,539,059 A | * | 7/1996 | Bierschenk | ........ | C08G 65/3322 562/605 |
| 6,136,331 A | * | 10/2000 | Morita | ..................... | A61K 8/86 424/401 |
| 8,513,459 B2 | * | 8/2013 | Ikeda | ................. | C08G 65/3236 562/864 |
| 2001/0050351 A1 | | 12/2001 | Saito et al. | | |
| 2007/0178133 A1 | | 8/2007 | Rolland | | |
| 2010/0101245 A1 | | 4/2010 | Bivens et al. | | |
| 2014/0123876 A1 | * | 5/2014 | Fontana | ................ | C07C 43/137 558/92 |
| 2014/0135244 A1 | | 5/2014 | Tonelli et al. | | |
| 2014/0243547 A1 | * | 8/2014 | Fontana | ................. | C08G 65/22 562/586 |

FOREIGN PATENT DOCUMENTS

| | | | | |
|---|---|---|---|---|
| JP | 53-132519 A | | 11/1978 | |
| JP | 60137928 A | * | 7/1985 | ............. C08G 65/18 |
| JP | 60202122 A | * | 10/1985 | ............. C08G 65/32 |
| JP | 2002-037880 A | | 2/2002 | |

(Continued)

OTHER PUBLICATIONS

International Preliminary Report on Patentability with the translation of Written Opinion dated Mar. 24, 2022 from the International Bureau in International application No. PCT/JP2020/032914.
Extended European Search Report dated Jul. 27, 2023 in European Application No. 20864031.8.
E. J. Soloski, et al., "Synthesis of Perfluoro (Polyether) Difunctional Compounds", Journal of Fluorine Chemistry, 1978, pp. 601-612, vol. 11 (12 pages total).
International Search Report for PCT/JP2020/032914 dated Nov. 17, 2020 [PCT/ISA/210].

*Primary Examiner* — Rip A Lee

(74) *Attorney, Agent, or Firm* — Sughrue Mion, PLLC

(57) ABSTRACT

A fluoropolyether-containing compound of the following formula (1a): $R^a$—$R^2$—$R^1$—$R^b$ (1a) wherein the symbols are as defined in the specification. Also disclosed is a fluoropolyether-containing compound of the following formula (1b): $R^a$—$R^{2'}$—$R^1$—$R^b$ (1b), as well as a method for producing a compound of the formula (A): FOC—$R^2$—$R^1$—COOR$^{12}$ (A) wherein the symbols are as defined in the specification.

10 Claims, No Drawings

(56) References Cited

FOREIGN PATENT DOCUMENTS

| | | | | |
|---|---|---|---|---|
| JP | 2009161532 A | * | 7/2009 | ............ C07C 59/135 |
| JP | 2010254738 A | * | 11/2010 | .......... C10M 133/46 |
| JP | 2014-517131 A | | 7/2014 | |
| JP | 2014520106 A | * | 8/2014 | ............. C07C 43/13 |
| RU | 2 461 599 C2 | | 9/2012 | |
| WO | WO-9003410 A1 | * | 4/1990 | ............. C08G 65/00 |
| WO | WO-0226686 A1 | * | 4/2002 | .......... B01F 17/0035 |
| WO | WO-0226687 A1 | * | 4/2002 | ............ C07C 41/18 |
| WO | WO-2013042732 A1 | * | 3/2013 | ............ C08G 65/007 |

\* cited by examiner

FLUOROPOLYETHER GROUP CONTAINING COMPOUND AND METHOD FOR PRODUCING THE SAME

CROSS-REFERENCE TO RELATED APPLICATIONS

This application is a Rule 53(b) Continuation of International Application No. PCT/JP2020/032914 filed Aug. 31, 2020, which claims priority based on Japanese Patent Application Nos. 2019-167534 filed Sep. 13, 2019, and 2020-008580 filed Jan. 22, 2020, the respective disclosures of which are incorporated herein by reference in their entireties.

TECHNICAL FIELD

The present disclosure relates to a fluoropolyether group-containing compound and a method for producing the same.

BACKGROUND ART

Fluoropolyether group-containing compounds are widely used as surface-treating agents, lubricants, and the like, and their applications have been further expanded.

Ring-opening polymerization of a cyclic ether such as tetrafluorooxetane or hexafluoropropylene oxide, for example, is known as one of the methods for producing a fluoropolyether group-containing compound. However, with such a method, a compound having a functional group only at one end of the molecular chain is usually obtained, and it is difficult to obtain a compound having a functional group at both ends of the molecular chain.

CITATION LIST

Patent Literature

Patent Literature 1: JP 2002-37880 A

SUMMARY

A fluoropolyether-containing compound of the following formula (1a):

$$R^a\text{—}R^2\text{—}R^1\text{—}R^b \quad (1a)$$

wherein
- $R^a$ is COF, COOR$^{11}$, CH$_2$OH, or CHO;
- $R^b$ is COF, COOR$^{11}$, CH$_2$OH, or CHO;
- wherein, $R^a$ and $R^b$ are groups different from each other;
- $R^{11}$ is each independently a hydrogen atom or an alkyl group having 1 to 6 carbon atoms optionally substituted with fluorine;
- $R^1$ is an alkylene group having 2 to 10 carbon atoms optionally substituted with fluorine;
- $R^2$ is 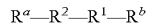—$R^{6a}$—(OR$^{5a}$)$_n$—O—;
- $R^{5a}$ is a linear or branched alkylene group having 2 to 10 carbon atoms optionally substituted with fluorine;
- $R^{6a}$ is a linear or branched alkylene group having 1 to 9 carbon atoms optionally substituted with fluorine; and
- n is an integer of 2 to 200.

Effect

According to the present disclosure, there is provided a novel fluoropolyether group-containing compound that can be used in various applications. Further, by using a specific initiator, a fluoropolyether group-containing compound having functional groups at both ends can be easily produced.

DESCRIPTION OF EMBODIMENTS

Hereinafter, a fluoropolyether group-containing compound of the present disclosure will be described in detail.

The present disclosure provides a fluoropolyether group-containing compound of the following formula (1):

$$R^a\text{—}R^2\text{—}R^1\text{—}R^b \quad (1)$$

wherein
- $R^a$ is COF, COOR$^{11}$, CH$_2$OH, or CHO;
- $R^b$ is COF, COOR$^{11}$, CH$_2$OH, or CHO;
- $R^{11}$ is an alkyl group having 1 to 6 carbon atoms optionally substituted with a hydrogen atom or fluorine;
- $R^1$ is an alkylene group having 2 to 10 carbon atoms optionally substituted with fluorine;
- $R^2$ is —$R^{6a}$—(OR$^{5a}$)$_n$—O—;
- $R^{5a}$ is a linear or branched alkylene group having 2 to 10 carbon atoms optionally substituted with fluorine;
- $R^{6a}$ is a linear or branched alkylene group having 1 to 9 carbon atoms optionally substituted with fluorine; and
- n is an integer of 2 to 200.

In one embodiment, the present disclosure provides a fluoropolyether group-containing compound of the following formula (1a):

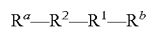

$$R^a\text{—}R^2\text{—}R^1\text{—}R^b \quad (1a)$$

wherein
- $R^a$ is COF, COOR$^{11}$, CH$_2$OH, or CHO;
- $R^b$ is COF, COOR$^{11}$, CH$_2$OH, or CHO;
- wherein, $R^a$ and $R^b$ are groups different from each other;
- $R^{11}$ is each independently a hydrogen atom or an alkyl group having 1 to 6 carbon atoms optionally substituted with fluorine;
- $R^1$ is an alkylene group having 2 to 10 carbon atoms optionally substituted with fluorine;
- $R^2$ is —$R^{6a}$—(OR$^{5a}$)$_n$—O—;
- $R^{5a}$ is a linear or branched alkylene group having 2 to 10 carbon atoms optionally substituted with fluorine;
- $R^{6a}$ is a linear or branched alkylene group having 1 to 9 carbon atoms optionally substituted with fluorine; and
- n is an integer of 2 to 200.

In one embodiment, the present disclosure provides a fluoropolyether group-containing compound of the following formula (1b):

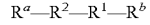

$$R^a\text{—}R^2\text{—}R^1\text{—}R^b \quad (1b):$$

wherein
- $R^a$ is COF, COOR$^{11}$, CH$_2$OH, or CHO;
- $R^b$ is COF, COOR$^{11}$, CH$_2$OH, or CHO;
- $R^{11}$ is each independently a hydrogen atom or an alkyl group having 1 to 6 carbon atoms optionally substituted with fluorine;
- $R^1$ is an alkylene group having 2 to 10 carbon atoms optionally substituted with fluorine;
- $R^2$ is —$R^{6a}$—(OR$^{5a}$)$_n$—O—;
- $R^{5b}$ is CF$_2$CF(CF$_3$) or CF$_2$CF$_2$CH$_2$;
- $R^{6b}$ is CF(CF$_3$) or CF$_2$CH$_2$; and
- n is an integer of 2 to 200.

The formulas (1a) and (1b): are different in that $R^a$ and $R^b$ are different in the formula (1a), whereas $R^a$ and $R^b$ may be the same or different in the formula (1b), and in that $R^2$ is $R^2$ is —$R^{6a}$—(OR$^{5a}$)$_n$—O— in the formula (1a), whereas $R^{2'}$ is —$R^{6b}$—(OR$^{5b}$)$_n$—O— in the formula (1b).

In the formula, $R^a$ is COF, COOR$^{11}$, CH$_2$OH, or CHO, preferably COF or COOR$^{11}$, and more preferably COF.

In the formula, $R^a$ is COF, COOR$^{11}$, CH$_2$OH, or CHO, and preferably COOR$^{11}$.

In the formula, $R^{11}$ is each independently a hydrogen atom or an alkyl group having 1 to 6 carbon atoms optionally substituted with fluorine, and preferably an alkyl group 1 to 6 carbon atoms optionally substituted with fluorine. The alkyl group having 1 to 6 carbon atoms in $R^{11}$ is preferably an alkyl group having 1 to 3 carbon atoms, more preferably a methyl group or an ethyl group, and still more preferably a methyl group.

In the formula (1a), $R^a$ and $R^b$ are groups different from each other.

In the formula (1b), $R^a$ and $R^b$ may be the same group or groups different from each other. In one embodiment, $R^a$ and $R^b$ are the same group. In another embodiment, $R^a$ and $R^b$ are different groups.

In one embodiment, the combination of $R^a$ and $R^b$ is COF and COOR$^{11}$ or COOR$^{11}$ and COOR$^{11}$, and preferably COF and COOR$^{11}$.

In the formula (a), $R^1$ is an alkylene group having 2 to 10 carbon atoms optionally substituted with fluorine. The alkylene group having 2 to 10 carbon atoms in $R^1$ is preferably an alkylene group having 2 to 6 carbon atoms, more preferably an alkylene group having 2 to 3 carbon atoms, and still more preferably an alkylene group having 2 carbon atoms.

In one embodiment, the alkylene group in $R^1$ is a fluoroalkylene group, and preferably a perfluoroalkylene group.

In a preferred embodiment, $R^1$ is a linear perfluoroalkylene group having 1 to 3 carbon atoms, and more preferably —CF$_2$CF$_2$—.

In the formula (1a), $R^2$ is —R$^{6a}$—(OR$^{5a}$)$_n$—O—.

$R^{5a}$ is a linear or branched alkylene group having 2 to 10 carbon atoms optionally substituted with fluorine. The alkylene group having 2 to 10 carbon atoms is preferably an alkylene group having 2 to 6 carbon atoms, more preferably an alkylene group having 2 to 4 carbon atoms, and still more preferably an alkylene group having 3 carbon atoms.

In one embodiment, the alkylene group in $R^{5a}$ is linear.

In another embodiment, the alkylene group in $R^{5a}$ is branched.

In a preferred embodiment, $R^{5a}$ is CF$_2$CF$_2$CH$_2$, CF$_2$CF$_2$CF$_2$, or CF$_2$CF (CF$_3$), preferably CF$_2$CF$_2$CH$_2$ or CF$_2$CF(CF$_3$), and more preferably CF$_2$CF$_2$CH$_2$.

In the formula, $R^{6a}$ is a linear or branched alkylene group having 1 to 9 carbon atoms optionally substituted with fluorine. The alkylene group having 1 to 9 carbon atoms is preferably an alkylene group having 1 to 5 carbon atoms, more preferably an alkylene group having 1 to 3 carbon atoms, for example, an alkylene group having 1 or 2 carbon atoms.

In one embodiment, the alkylene group in $R^{6a}$ is linear.

In another embodiment, the alkylene group in $R^{6a}$ is branched.

In a preferred embodiment, $R^{6a}$ is CF$_2$CH$_2$, CF$_2$CF$_2$, or CF$_2$(CF$_3$), preferably CF$_2$CH$_2$ or CF$_2$(CF$_3$), and more preferably CF$_2$CH$_2$.

In one embodiment, the number of carbon atoms in the alkylene group of $R^{5a}$ is one greater than the number of carbon atoms in the alkylene group of $R^{6a}$. For example, when the number of carbon atoms of the alkylene group in $R^{5a}$ is 3, the number of carbon atoms of the alkylene group in $R^{6a}$ is 2.

In the formula (1b), $R^{2'}$ is —R$^{6a}$—(OR$^{5a}$)$_n$—O—.

In the formula (1b), $R^{5b}$ is CF$_2$CF(CF$_3$) or CF$_2$CF$_2$CH$_2$.

In the formula (1b), $R^{6b}$ is CF(CF$_3$) or CF$_2$CH$_2$.

In one embodiment, $R^{5b}$ is CF$_2$CF(CF$_3$) and $R^{6b}$ is CF(CF$_3$).

In another embodiment, $R^{5b}$ is CF$_2$CF$_2$CH$_2$ and $R^{6b}$ is CF$_2$CH$_2$.

In the formula, n is an integer of 2 to 200, preferably an integer of 5 to 100, and more preferably an integer of 10 to 60.

In a preferred embodiment, in the fluoropolyether group-containing compound of the formula (1a) of the present disclosure,
$R^a$ is the COF;
$R^b$ is COOR$^{11}$;
$R^{11}$ is an alkylene group having 1 to 6 carbon atoms optionally substituted with fluorine;
$R^1$ is a fluoroalkylene group having 2 to 6 carbon atoms;
$R^2$ is —R$^{6a}$—(OR$^{5a}$)$_n$—O—;
$R^{5a}$ is a linear or branched fluoroalkylene group having 2 to 4 carbon atoms;
$R^{6a}$ is a linear or branched alkylene group having 1 to 3 carbon atoms optionally substituted with fluorine; and
n is an integer of 5 to 100.

In a more preferred embodiment, in the fluoropolyether group-containing compound of the formula (1a) of the present disclosure,
$R^a$ is the COF;
$R^b$ is COOR$^{11}$;
$R^{11}$ is an alkylene group having 1 to 6 carbon atoms optionally substituted with fluorine;
$R^1$ is a fluoroalkylene group having 2 to 6 carbon atoms;
$R^2$ is —CF$_2$CH$_2$—(OCF$_2$CF$_2$CH$_2$)$_n$—O— or —CF(CF$_3$)—(OCF$_2$CF(CF$_3$))$_n$—O—; and
n is an integer of 5 to 100.

In a preferred embodiment, in the fluoropolyether group-containing compound of the formula (1b): of the present disclosure,
$R^a$ is COF or COOR$^{11}$;
$R^b$ is COOR$^{11}$;
$R^{11}$ is an alkyl group having 1 to 6 carbon atoms;
$R^1$ is a fluoroalkylene group having 2 to 6 carbon atoms;
$R^{2'}$ is —R$^{6a}$—(OR$^{5a}$)$_n$—O—;
$R^{5b}$ is CF$_2$CF (CF$_3$) or CF$_2$CF$_2$CH$_2$;
$R^{6b}$ is CF(CF$_3$) or CF$_2$CH$_2$; and
n is an integer of 5 to 100.

In one embodiment, the number-average molecular weight of the fluoropolyether group-containing compound is not limited, but may be, for example, 500 or more, preferably 1,000 or more, for example 3,000 or more, 5,000 or more, or 10,000 or more. The number-average molecular weight of the fluoropolyether group-containing compound is not limited, but may be, for example, 100,000 or less, 50,000 or less, 30,000 or less, 10,000 or less, or 5,000 or less.

In one embodiment, the dispersion (weight-average molecular weight/number-average molecular weight) of the fluoropolyether group-containing compound is not limited, but may preferably be 1.5 or less, more preferably 1.3 or less, still more preferably 1.2 or less, and particularly preferably 1.1 or less.

The number-average molecular weight and the weight-average molecular weight can be determined by F-NMR, and may also be determined by GPC.

The present disclosure provides a composition containing two or more compounds of the formula (1).

In one embodiment, the compound of the formula (1) is a fluoropolyether group-containing compound of the formula (1a) or a fluoropolyether group-containing compound of the formula (1b).

In one embodiment, two or more compounds in the composition have different structures in $R^a$ and/or $R^b$. For example, $R^b$ may be —COO-alkyl in one compound and $R^b$ may be —COOH in the other compound.

The fluoropolyether group-containing compound of the present disclosure can be suitably used as a surface-treating agent, a lubricating oil, and the like, and an intermediate thereof.

The present disclosure provides a method for producing the fluoropolyether group-containing compound.

That is, the present disclosure provides a method for producing a compound of the formula (A):

$$\text{FOC—}R^2\text{—}R^2\text{—COOR}^{12} \quad (A)$$

wherein
$R^1$ is an alkylene group having 2 to 10 carbon atoms optionally substituted with fluorine;
$R^2$ is —$R^{6a}$—$(OR^{5a})_n$—O—;
$R^5$ is a linear or branched alkylene group having 2 to 10 carbon atoms optionally substituted with fluorine;
$R^6$ is a linear or branched alkylene group having 1 to 9 carbon atoms optionally substituted with fluorine; and
$R^{12}$ is an alkyl group having 1 to 6 carbon atoms optionally substituted with fluorine,
the method comprising:
reacting an acid fluoride compound of the formula (a):

$$\text{FOC—}R^{13}\text{—COOR}^{12} \quad (a)$$

wherein
$R^{13}$ is an alkylene group having 1 to 9 carbon atoms optionally substituted with fluorine; and
$R^{12}$ is an alkyl group having 1 to 6 carbon atoms optionally substituted with fluorine,
with a cyclic ether compound of the formula (b):

(b)

wherein $R^{15}$ is a linear or branched alkylene group having 2 to 10 carbon atoms optionally substituted with fluorine.

According to the method of the present disclosure, the cyclic ether of the formula (b) is bonded to the COF side of the acid fluoride compound of the formula (a). That is, in the method of the present disclosure, the reaction proceeds at one end side of the acid fluoride compound of the formula (a), and the polymer chain extends at such an end. Therefore, it is possible to obtain a compound having a different functional group, that is, one of COF and $COOR^{12}$, at each end of the polymer chain. Further, the production method of the present disclosure facilitates the adjustment of the degree of polymerization, molecular weight, degree of dispersion, or the like, for example, to obtain a compound with the desired molecular weight or to obtain a compound with a small degree of dispersion, because the reaction is easily controlled.

The formula (A) corresponds to the formula (1) in which $R^a$ is COF and $R^b$ is $COOR^{11}$ (where RH is an alkyl group having 1 to 6 carbon atoms), and among the symbols of the formula (A), $R^1$ and $R^2$ have the same meaning as the description of the formula (1).

In the formula (A), $R^{12}$ corresponds to RH of the formula (1) and is an alkyl group having 1 to 6 carbon atoms optionally substituted with fluorine. The alkyl group having 1 to 6 carbon atoms in $R^{12}$ is preferably an alkyl group having 1 to 3 carbon atoms, more preferably a methyl group or an ethyl group, and still more preferably a methyl group. In one embodiment, the alkyl group is substituted with fluorine and is preferably a perfluoroalkyl group. In another embodiment, the alkyl group is not substituted.

In the formula (a), $R^{12}$ is an alkyl group having 1 to 6 carbon atoms optionally substituted with fluorine, and has the same meaning as described above.

In the formula (a), $R^{13}$ is an alkylene group having 1 to 9 carbon atoms optionally substituted with fluorine. $R^1$ of the formula (A) corresponds to a group in which a carbon atom derived from COF of the formula (a) is bonded to the left end of $R^{13}$.

The alkylene group having 1 to 9 carbon atoms in $R^{13}$ is preferably an alkylene group having 1 to 5 carbon atoms, more preferably an alkylene group having 1 to 2 carbon atoms, and still more preferably methylene.

In one embodiment, the alkylene group in $R^{13}$ is a fluoroalkylene group, and preferably a perfluoroalkylene group.

In a preferred embodiment, $R^{13}$ is a linear perfluoroalkylene group having 1 to 2 carbon atoms, and more preferably —$CF_2$—.

The acid fluoride compound of the formula (a) functions as a polymerization initiator in the reaction.

The acid fluoride compound of the formula (a) is commercially available or can be produced by a method known to those skilled in the art.

In the formula (b), $R^{15}$ is an alkylene group having 1 to 10 carbon atoms optionally substituted with fluorine. The alkylene group having 2 to 10 carbon atoms in $R^{15}$ is preferably an alkylene group having 2 to 6 carbon atoms, more preferably an alkylene group having 2 to 4 carbon atoms, and still more preferably an alkylene group having 3 carbon atoms.

In one embodiment, the alkylene group in $R^{15}$ is linear. In another embodiment, the alkylene group in $R^{15}$ is branched.

In a preferred embodiment, $R^{15}$ is $CF_2CF_2CH_2$, $CF_2CF_2CF_2$, or $CF_2CF$ ($CF_3$), preferably $CF_2CF_2CH_2$ or $CF_2CF(CF_3)$, and more preferably $CF_2CF_2CH_2$.

In a preferred embodiment, the cyclic ether compound of the formula (b) is tetrafluorooxetane or hexafluoropropylene oxide, more preferably tetrafluorooxetane.

The cyclic ether compound of the formula (b) is cleaved between C and O to react with the acid fluoride compound of the above formula (a), resulting in the fluoropolyether group-containing compound of the formula (A). That is, the compound of the formula (b) forms a portion of $R^2$ of the formula (A), which is a product.

The cyclic ether compound of the formula (b) functions as a monomer in the reaction.

The cyclic ether compound of the formula (b) is commercially available or can be produced by a method known to those skilled in the art.

The proportion of the acid fluoride compound of the formula (a) to the cyclic ether compound of the formula (b) can be appropriately set according to the molecular weight of the target compound and the like, and for example, the molar ratio may be 0.01:100 to 10:100, preferably 0.1:100 to 5:100, and for example, 1:100 to 5:100.

The reaction between the acid fluoride compound of the formula (a) and the cyclic ether compound of the formula (b) is usually carried out in a solvent. Examples of the solvent include cyclic ethers such as tetrahydrofuran (THF), tetrahydropyran, and dioxane, cyclic ethers such as diethyl ether, diisopropyl ether, dibutyl ether, monoglyme, diglyme, triglyme, and tetraglyme, aromatic compounds such as HMPA (hexamethylphosphamide), dimethylpropylene (DMPU), tetramethylethylenediamine (TMEDA), toluene, xylene, and benzotrifluorides, amides such as N,N-dimethylformamide, N,N-dimethylacetamide, and N-methylpyrrolidone, and fluorine-containing organic solvents such as hexafluoropropylene, trichlorotrifluoroethane, 1,1,1,3,3-pentafluorobutane, m-xylene hexafluorolide, perfluorohexane, perfluorooctane, perfluorodimethylcyclohexane, perfluorodecalin, perfluoroalkyl ethanol, perfluorobenzene, perfluorotoluene, perfluoroalkylamine (such as fluorinert (trade name)), perfluoroalkyl ether, perfluorobutyl tetrahydrofuran, polyfluoroaliphatic hydrocarbon (AsahiKlin AC6000 (trade name)), hydrochlorofluorocarbon (such as AsahiKlin AK-225 (trade name)), hydrofluoroether (such as Novec (trade name), HFE-7100 (trade name)), 1,1,2,2,3,3,4-heptafluorocyclopentane, fluorinated alcohol, perfluoroalkyl bromide, perfluoroalkyl iodide, perfluoropolyester (such as Krytox (trade name), Demnum (trade name), Fomblin (trade name)), 1,3-bistrifluoromethylbenzene, 2-(perfluoroalkyl)ethyl methacrylate, 2-(perfluoroalkyl)ethyl acrylate, perfluoroalkyl ethylene, Freon 134a, and hexafluoropropene oligomers, or mixtures thereof.

The above reaction is preferably carried out in the presence of a catalyst. Examples of the catalyst include, but are not limited to, inorganic bases such as NaH, CaH$_2$, LiH, LiAlH$_4$, NaBH$_4$, Cs$^t$OBu, K$^t$OBu, Na$^t$OBu, Li$^t$OBu, CsOH, KOH, NaOH, LiOH, Cs$_2$CO$_3$, K$_2$CO$_3$, Na$_2$CO$_3$, Li$_2$CO$_3$, CsHCO$_3$, KHCO$_3$, NaHCO$_3$, LiHCO$_3$, KF, CsF, tetra-n-butylammonium fluoride (TBAF), organic bases such as triethylamine, pyridine, N,N-dimethyl-4-aminopyridine (DMAP), diazabicycloundecene (DBU) and 1,4-diazabicyclo[2.2.2]octane (DABCO), and organic lithium reagents such as $^n$BuLi, $^t$BuLi, and lithium diisopropylamide (LDA).

The reaction temperature of the above reaction is usually −80° C. to 60° C., preferably −60° C. to 40° C., and more preferably −50° C. to 30° C.

The reaction time of the above reaction may usually be 1 hour to 5 days, for example 1 to 3 days.

The end functional group of the fluoropolyether group-containing compound of formula (A) can be converted into a desired functional group by an appropriate treatment. For example, the end functional group can be converted into COOR$^{11}$ by reacting alcohol HOR$^{11}$, and the end functional group can be converted into CH$_2$OH, CHO, or the like by reducing the terminal functional group, whereby the compound of the formula (1) can be obtained.

Further, the fluoropolyether group-containing compound of the formula (A) can be fluorinated. For example, the hydrogen atom bonded to the carbon of the fluoropolyether group-containing compound can be fluorinated and converted into the perfluoropolyether group-containing compound.

The present disclosure includes the following embodiments.

[1] A fluoropolyether-containing compound of the following formula (1a):

$$R^a—R^2—R^1—R^b \qquad (1a)$$

wherein
R$^a$ is COF, COOR$^{11}$, CH$_2$OH, or CHO;
R$^b$ is COF, COOR$^{11}$, CH$_2$OH, or CHO;
wherein, R$^a$ and R$^b$ are groups different from each other;
R$^{11}$ is each independently a hydrogen atom or an alkyl group having 1 to 6 carbon atoms optionally substituted with fluorine;
R$^1$ is an alkylene group having 2 to 10 carbon atoms optionally substituted with fluorine;
R$^2$ is —R$^{6a}$—(OR$^{5a}$)$_n$—O—;
R$^{5a}$ is a linear or branched alkylene group having 2 to 10 carbon atoms optionally substituted with fluorine;
R$^{6a}$ is a linear or branched alkylene group having 1 to 9 carbon atoms optionally substituted with fluorine; and
n is an integer of 2 to 200.

[2] The fluoropolyether-containing compound according to [1],
wherein R$^{5a}$ is a linear or branched alkylene group having 2 to 4 carbon atoms optionally substituted with fluorine; and
R$^{6a}$ is a linear or branched alkylene group having 1 to 3 carbon atoms optionally substituted with fluorine.

[3] The fluoropolyether-containing compound according to [1] or [2],
wherein R$^{5a}$ is an alkylene group having 3 carbon atoms optionally substituted with fluorine; and
R$^{6a}$ is an alkylene group having 2 carbon atoms optionally substituted with fluorine.

[4] A fluoropolyether-containing compound of the following formula (1b):

$$R^a—R^{2'}—R^1—R^b \qquad (1b):$$

wherein
R$^a$ is COF, COOR$^{11}$, CH$_2$OH, or CHO;
R$^b$ is COF, COOR$^{11}$, CH$_2$OH, or CHO;
R$^{11}$ is each independently a hydrogen atom or an alkyl group having 1 to 6 carbon atoms optionally substituted with fluorine;
R$^1$ is an alkylene group having 2 to 10 carbon atoms optionally substituted with fluorine;
R$^{2'}$ is —R$^{6a}$—(OR$^{5a}$)$_n$—O—;
R$^{5b}$ is CF$_2$CF (CF$_3$) or CF$_2$CF$_2$CH$_2$;
R$^{6b}$ is CF(CF$_3$) or CF$_2$CH$_2$; and
n is an integer of 2 to 200.

[5] The fluoropolyether group-containing compound according to any one of [1] to [4], wherein R$^a$ is COF, R$^b$ is COOR$^{11}$, and R$^{11}$ is an alkyl group having 1 to 6 carbon atoms.

[6] The fluoropolyether group-containing compound according to any one of [1] to [5], wherein R$^1$ is a perfluoroalkylene group having 2 to 10 carbon atoms.

[7] A method for producing a compound of the formula (A):

$$FOC—R^2—R^1—COOR^{12} \qquad (A)$$

wherein
R$^1$ is an alkylene group having 2 to 10 carbon atoms optionally substituted with fluorine;
R$^2$ is —R$^{6a}$—(OR$^{5a}$)$_n$—O—;
R$^5$ is a linear or branched alkylene group having 2 to 10 carbon atoms optionally substituted with fluorine;
R$^6$ is a linear or branched alkylene group having 1 to 9 carbon atoms optionally substituted with fluorine;
R$^{12}$ is an alkyl group having 1 to 6 carbon atoms optionally substituted with fluorine, and
n is an integer of 2 to 200,
the method comprising:
reacting an acid fluoride compound of the formula (a):

$$FOC—R^{13}—COOR^{12} \qquad (a)$$

wherein
R$^{13}$ is an alkylene group having 1 to 9 carbon atoms optionally substituted with fluorine; and
R$^{12}$ is an alkyl group having 1 to 6 carbon atoms optionally substituted with fluorine,
with a cyclic ether compound of the formula (b):

(b)

wherein R$^{15}$ is a linear or branched alkylene group having 2 to 10 carbon atoms optionally substituted with fluorine.

[8] The production method according to [7], wherein R$^{13}$ is a perfluoroalkylene group having 1 to 9 carbon atoms.

[9] The production method according to [7] or [8], wherein R$^{15}$ is a linear or branched alkylene group having 2 to 4 carbon atoms optionally substituted with fluorine.

[10] The production method according to any one of [7] to [9], wherein R$^{15}$ is $CF_2CF_2CH_2$ or $CF_2CF(CF_3)$.

EXAMPLES

Example 1: (Synthesis of Compound A1)

To a nitrogen-purged reaction container, 27.3 g of cesium fluoride, 662 mL of diglyme, and 198.2 g of methyl 2,2,3-trifluoro-3-oxopropanoate were added, and the mixture was stirred at 5° C. for 10 minutes under an ice bath. Subsequently, at 5° C. under the ice bath, 892.2 g of 2,2,3,3-tetrafluorooxetane was added dropwise from the dropping funnel to the reaction container over 20 minutes and stirred for 2 hours. Then, the ice bath was removed and the mixture was stirred for 48 hours. The obtained reaction solution was filtered under pressure with a 5 μm PTFE filter, and diglyme was evaporated to obtain compound A1.

(Number-average molecular weight: 912 (NMR), initiation efficiency from the acid fluoride: 100%)
$^{19}$F-NMR Assignment of Compound A1

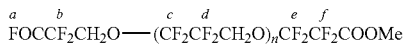

Chemical shift is based on m-xylene hexafluoride standard (−80.0 ppm)
a: 3.5 ppm, b: −130.3 ppm, c: −106.9 to −106.2 ppm, d: −140.4 to −140.7 ppm, e: −106.0 ppm, f: −137.9 ppm Example 2: (Synthesis of Compound A2)

To a nitrogen-purged reaction container, 15.4 g of cesium fluoride, 290 mL of diglyme, and 107.0 g of methyl 2,2,3-trifluoro-3-oxopropanoate were added, and the mixture was stirred at 5° C. for 10 minutes under an ice bath. Subsequently, at 5° C. under the ice bath, 526.0 g of 2,2,3,3-tetrafluorooxetane was added dropwise from the dropping funnel to the reaction container over 20 minutes and stirred for 2 hours. Then, the ice bath was removed and the mixture was stirred for 50 hours. To the obtained reaction solution, 60 mL of methanol was added dropwise over 20 minutes, and the mixture was stirred for 24 hours. After evaporating volatile contents from the reaction solution under reduced pressure, 80 g of m-xylene hexaflorlde and 40 g of water were added for separation and washing, and 5 g of magnesium sulfate was added to the extracted organic layer for drying. Volatile contents were evaporated from the resulting treated solution to obtain compound A2.

(Number-average molecular weight: 865 (NMR), initiation efficiency from the acid fluoride: 100%)
$^{19}$F-NMR Assignment of Compound A2

Chemical shift is based on m-xylene hexafluoride standard (−80.0 ppm)
b: −131.0 ppm, c: −106.4 to −106.8 ppm, d: −140.7 ppm, e: −106.0 ppm, f: −138.0 ppm Example 3: (Synthesis of Compound B1)

To a nitrogen-purged reaction container, 4.23 g of cesium fluoride, 101 g of tetraglyme, and 4.22 g of methyl 2,2,3-trifluoro-3-oxopropanoate were added, and the mixture was stirred at 0° C. for 2 hours. Subsequently, a total of 200 g of hexafluoropropylene oxide was added in 10 g increments over 60 minutes at 0° C., and the mixture was then stirred. The obtained reaction solution was filtered under pressure with a 5 μm PTFE filter, and tetraglyme was evaporated to obtain compound B1 (COF and methyl ester).

(Number-average molecular weight: 2,000 (NMR), initiation efficiency from the acid fluoride: 40%)
$^{19}$F-NMR Assignment of Compound B1

Chemical shift is based on m-xylene hexafluoride standard (−65.0 ppm)
a: −122.4 ppm, c: −145.9 to −146.3 ppm, d,e: −79.5 to −83.3 ppm, f: −131.0 ppm, g: −82.2 to −82.6 ppm, h: 25.0 ppm Example 4: (Synthesis of Compound B2)

To the obtained B1 reaction solution, 10 mL of methanol was added dropwise over 5 minutes at 0° C., and the mixture was stirred for 2 hours. For separation and washing, 130 g of m-xylene hexafloride and 200 g of water were added, and 5 g of magnesium sulfate was added to the extracted organic layer for drying. Volatile contents were evaporated from the resulting treated solution to obtain compound B2 (methyl ester at both ends).

(Number-average molecular weight: 2,000 (NMR), initiation efficiency from the acid fluoride: 40%)
$^{19}$F-NMR Assignment of Compound B2

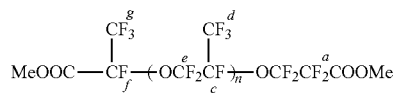

Chemical shift is based on m-xylene hexafluoride standard (−65.0 ppm)

a: −122.5 ppm, c: −145.4 to −146.2 ppm, d,e: −79.6 to −82.5 ppm, f: −132.5 ppm, g: −83.7 to −84.1 ppm Example 5: (Synthesis of Compound B3)

To a nitrogen-purged reaction container, 3.85 g of cesium fluoride, 100 g of tetraglyme, and 3.98 g of methyl 2,2,3-trifluoro-3-oxopropanoate were added, and the mixture was stirred at 0° C. for 2 hours. Subsequently, a total of 200 g of hexafluoropropylene oxide was added in 5 g increments over 60 minutes at −30° C., and the mixture was then stirred. To the obtained reaction solution, 10 mL of methanol was added dropwise over 5 minutes at 0° C., and the mixture was stirred for 2 hours. For separation and washing, 130 g of m-xylene hexafloride and 200 g of water were added, and 5 g of magnesium sulfate was added to the extracted organic layer for drying. Volatile contents were evaporated from the resulting treated solution to obtain compound B3 (methyl ester at both ends).

(Number-average molecular weight: 3,000 (NMR), initiation efficiency from the acid fluoride: 70%)

Example 6: (Synthesis of Compound B4)

To a nitrogen-purged reaction container, 1.94 g of potassium fluoride, 13 g of tetraglyme, 130 g of m-xylene hexafloride, and 5.20 g of methyl 2,2,3-trifluoro-3-oxopropanoate were added, and the mixture was stirred at 0° C. for 2 hours. Subsequently, a total of 140 g of hexafluoropropylene oxide was added in 10 g increments over 60 minutes at 0° C., and the mixture was then stirred. The obtained reaction solution was filtered under pressure with a 5 μm PTFE filter, and tetraglyme was evaporated to obtain compound B4 (COF and methyl ester).

(Number-average molecular weight: 2,900 (NMR), initiation efficiency from the acid fluoride: 60%, Mw/Mn=1.07 (GPC))

Example 7: (Synthesis of Compound B5)

To the obtained B4 reaction solution, 10 mL of methanol was added dropwise over 5 minutes at 0° C., and the mixture was stirred for 2 hours. For separation and washing, 200 g of water was added, and 5 g of magnesium sulfate was added to the extracted organic layer for drying. Volatile contents were evaporated from the resulting treated solution to obtain compound B5 (methyl ester at both ends).

(Number-average molecular weight: 2,900 (NMR), initiation efficiency from the acid fluoride: 60%)

Example 8: (Synthesis of Compound B6)

To a nitrogen-purged reaction container, 1.87 g of potassium fluoride, 13 g of tetraglyme, 130 g of m-xylene hexafloride, and 5.15 g of methyl 2,2,3-trifluoro-3-oxopropanoate were added, and the mixture was stirred at 0° C. for 2 hours. Subsequently, a total of 140 g of hexafluoropropylene oxide was added in 5 g increments over 60 minutes at −30° C., and the mixture was then stirred. To the obtained reaction solution, 10 mL of methanol was added dropwise over 5 minutes at 0° C., and the mixture was stirred for 2 hours. To the reaction solution, 200 g of water was added for separation and washing, and 5 g of magnesium sulfate was added to the extracted organic layer for drying. Volatile contents were evaporated from the resulting treated solution to obtain compound B6 (methyl ester at both ends).

(Number-average molecular weight: 4,000 (NMR), initiation efficiency from the acid fluoride: 86%)

Example 9: (Synthesis of Compound B7)

To a nitrogen-purged reaction container, 4.23 g of cesium fluoride, 11 g of tetraglyme, 120 g of m-xylene hexafloride, and 4.22 g of methyl 2,2,3-trifluoro-3-oxopropanoate were added, and the mixture was stirred at 0° C. for 2 hours. Subsequently, a total of 200 g of hexafluoropropylene oxide was added in 10 g increments over 60 minutes at 0° C., and the mixture was then stirred. To the obtained reaction solution, 10 mL of methanol was added dropwise over 5 minutes at 0° C., and the mixture was stirred for 2 hours. To the reaction solution, 200 g of water was added for separation and washing, and 5 g of magnesium sulfate was added to the extracted organic layer for drying. Volatile contents were evaporated from the resulting treated solution to obtain compound B7 (methyl ester at both ends).

(Number-average molecular weight: 3,500 (NMR), initiation efficiency from the acid fluoride: 43%)

Example 10: (Synthesis of Compound B8)

To a nitrogen-purged reaction container, 4.23 g of cesium fluoride, 11 g of tetraglyme, 120 g of Novec 7200 (manufactured by 3M), and 4.22 g of methyl 2,2,3-trifluoro-3-oxopropanoate were added, and the mixture was stirred at 0° C. for 2 hours. Subsequently, a total of 200 g of hexafluoropropylene oxide was added in 10 g increments over 60 minutes at 0° C., and the mixture was then stirred. To the obtained reaction solution, 10 mL of methanol was added dropwise over 5 minutes at 0° C., and the mixture was stirred for 2 hours. To the reaction solution, 200 g of water was added for separation and washing, and 5 g of magnesium sulfate was added to the extracted organic layer for drying. Volatile contents were evaporated from the resulting treated solution to obtain compound B8 (methyl ester at both ends).

(Number-average molecular weight: 3,400 (NMR), initiation efficiency from the acid fluoride: 45%)

Example 11: (Synthesis of Compound B9)

To a nitrogen-purged reaction container, 4.23 g of cesium fluoride, 11 g of tetraglyme, 135 g of Novec 7100 (manufactured by 3M), and 4.22 g of methyl 2,2,3-trifluoro-3-oxopropanoate were added, and the mixture was stirred at 0° C. for 2 hours. Subsequently, a total of 200 g of hexafluoropropylene oxide was added in 10 g increments over 60 minutes at 0° C., and the mixture was then stirred. To the obtained reaction solution, 10 mL of methanol was added dropwise over 5 minutes at 0° C., and the mixture was stirred for 2 hours. To the reaction solution, 200 g of water was added for separation and washing, and 5 g of magnesium sulfate was added to the extracted organic layer for drying. Volatile contents were evaporated from the resulting treated solution to obtain compound B9 (methyl ester at both ends).

(Number-average molecular weight: 3,500 (NMR), initiation efficiency from the acid fluoride: 45%)

Example 12: (Synthesis of Compound B10)

To a nitrogen-purged reaction container, 4.23 g of cesium fluoride, 11 g of tetraglyme, 115 g of 1,1,1,3,3-pentafluorobutane, and 4.22 g of methyl 2,2,3-trifluoro-3-oxopropanoate were added, and the mixture was stirred at 0° C. for 2 hours. Subsequently, a total of 200 g of hexafluoropropylene oxide was added in 10 g increments over 60 minutes at 0° C., and the mixture was then stirred. To the obtained reaction solution, 10 mL of methanol was added dropwise over 5 minutes at 0° C., and the mixture was stirred for 2 hours. To the reaction solution, 200 g of water was added for separation and washing, and 5 g of magnesium sulfate was added to the extracted organic layer for drying. Volatile contents were evaporated from the resulting treated solution to obtain compound B10 (methyl ester at both ends).

(Number-average molecular weight: 2,500 (NMR), initiation efficiency from the acid fluoride: 40%)

Example 13: (Synthesis of Compound B11)

To a nitrogen-purged reaction container, 2.9 g of potassium fluoride, 101 g of tetraglyme, and 9 g of methyl 2,2,3-trifluoro-3-oxopropanoate were added, and the mixture was stirred at 0° C. for 2 hours. Subsequently, a total of 200 g of hexafluoropropylene oxide was added in 10 g increments over 60 minutes at 0° C., and the mixture was then stirred. To the obtained reaction solution, 10 mL of methanol was added dropwise over 5 minutes at 0° C., and the mixture was stirred for 2 hours. To the reaction solution, 200 g of water was added for separation and washing, and 5 g of magnesium sulfate was added to the extracted organic layer for drying. Volatile contents were evaporated from the resulting treated solution to obtain compound B11 (methyl ester at both ends).

(Number-average molecular weight: 900 (NMR), initiation efficiency from the acid fluoride: 74%)

Example 14: (Synthesis of Compound B12)

To a nitrogen-purged reaction container, 2.9 g of potassium fluoride, 20 g of tetraglyme, 120 g of m-xylene hexafloride, and 9 g of methyl 2,2,3-trifluoro-3-oxopropanoate were added, and the mixture was stirred at 0° C. for 2 hours. Subsequently, a total of 200 g of hexafluoropropylene oxide was added in 10 g increments over 60 minutes at 0° C., and the mixture was then stirred. To the obtained reaction solution, 10 mL of methanol was added dropwise over 5 minutes at 0° C., and the mixture was stirred for 2 hours. To the reaction solution, 200 g of water was added for separation and washing, and 5 g of magnesium sulfate was added to the extracted organic layer for drying. Volatile contents were evaporated from the resulting treated solution to obtain compound B12 (methyl ester at both ends).

(Number-average molecular weight: 2,100 (NMR), initiation efficiency from the acid fluoride: 76%)

Example 15: (Synthesis of Compound B13)

To a nitrogen-purged reaction container, 2.9 g of potassium fluoride, 20 g of tetraglyme, 120 g of Novec 7200 (manufactured by 3M), and 9 g of methyl 2,2,3-trifluoro-3-oxopropanoate were added, and the mixture was stirred at 0° C. for 2 hours. Subsequently, a total of 200 g of hexafluoropropylene oxide was added in 10 g increments over 60 minutes at 0° C., and the mixture was then stirred. To the obtained reaction solution, 10 mL of methanol was added dropwise over 5 minutes at 0° C., and the mixture was stirred for 2 hours. To the reaction solution, 200 g of water was added for separation and washing, and 5 g of magnesium sulfate was added to the extracted organic layer for drying. Volatile contents were evaporated from the resulting treated solution to obtain compound B13 (methyl ester at both ends).

(Number-average molecular weight: 1,900 (NMR), initiation efficiency from the acid fluoride: 75%)

INDUSTRIAL APPLICABILITY

According to the production method of the present disclosure, a fluoropolyether group-containing compound having functional groups at both ends can be easily produced.

What is claimed is:

1. A fluoropolyether-containing compound of the following formula (1a):

(1a)

wherein
$R^a$ is COF, COOR$^{11}$, CH$_2$OH, or CHO;
$R^b$ is COF, COOR$^{11}$, CH$_2$OH, or CHO;
wherein $R^a$ and $R^b$ are groups different from each other;
$R^{11}$ is each independently a hydrogen atom or an alkyl group having 1 to 6 carbon atoms optionally substituted with fluorine;
$R^1$ is a perfluoroalkylene group having 2 to 10 carbon atoms;

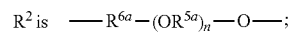

$R^{5a}$ is CF$_2$CF$_2$CH$_2$;
$R^{6a}$ is a linear alkylene group having 1 to 9 carbon atoms substituted with fluorine; and
n is an integer of 2 to 200.

2. The fluoropolyether-containing compound according to claim 1,
wherein $R^{6a}$ is a linear alkylene group having 1 to 3 carbon atoms substituted with fluorine.

3. The fluoropolyether-containing compound according to claim 1,
wherein $R^{6a}$ is a linear alkylene group having 2 carbon atoms substituted with fluorine.

4. The fluoropolyether group-containing compound according to claim 1, wherein $R^a$ is COF, $R^b$ is COOR$^{11}$, and $R^{11}$ is an alkyl group having 1 to 6 carbon atoms.

5. The fluoropolyether group-containing compound according to claim 1, wherein $R^1$ is a perfluoroalkylene group having 2 to 6 carbon atoms.

6. A fluoropolyether-containing compound of the following formula (1b):

(1b)

wherein
$R^a$ is COF, COOR$^{11}$, CH$_2$OH, or CHO;
$R^b$ is COF, COOR$^{11}$, CH$_2$OH, or CHO;
provided that
if $R^a$ is COF or COOR$^{11}$, $R^b$ is CH$_2$OH or CHO, or
if $R^b$ is COF or COOR$^{11}$, $R^a$ is CH$_2$OH or CHO;

$R^{11}$ is each independently a hydrogen atom or an alkyl group having 1 to 6 carbon atoms optionally substituted with fluorine;

$R^1$ is an a perfluoroalkylene group having 2 to 10 carbon atoms;

$R^{2'}$ is —$R^{6b}$—(O$R^{5b}$)$_n$—O—;

$R^{5b}$ is $CF_2CF_2CH_2$;

$R^{6b}$ is $CF_2CH_2$; and n is an integer of 2 to 200.

7. A method for producing a compound of the formula (A):

$$FOC-R^2-R^1-COOR^{12} \quad (A)$$

wherein $R^1$ is a perfluoroalkylene group having 2 to 10 carbon atoms;

$R^2$ is —$R^6$—(O$R^5$)$_n$—O—;

$R^5$ is a linear alkylene group having 2 to 10 carbon atoms substituted with fluorine;

$R^6$ is a linear alkylene group having 1 to 9 carbon atoms substituted with fluorine;

$R^{12}$ is an alkyl group having 1 to 6 carbon atoms optionally substituted with fluorine; and n is an integer of 2 to 200, the method comprising:

reacting an acid fluoride compound of the formula (a):

$$FOC-R^{13}-COOR^{12} \quad (a)$$

wherein $R^{13}$ is an alkylene group having 1 to 9 carbon atoms optionally substituted with fluorine; and $R^{12}$ is an alkyl group having 1 to 6 carbon atoms optionally substituted with fluorine, with a cyclic ether compound of the formula (b):

(b)

wherein $R^{15}$ is a linear alkylene group having 2 to 10 carbon atoms substituted with fluorine.

8. The production method according to claim 7, wherein $R^{13}$ is a perfluoroalkylene group having 1 to 9 carbon atoms.

9. The production method according to claim 7, wherein $R^{15}$ is a linear alkylene group having 2 to 4 carbon atoms substituted with fluorine.

10. The production method according to claim 7, wherein $R^{15}$ is $CF_2CF_2CH_2$.

* * * * *